United States Patent [19]

Perronnet et al.

[11] 4,014,679
[45] Mar. 29, 1977

[54] NOVEL CROTONANILIDES

[75] Inventors: Jacques Perronnet; Pierre Girault, both of Paris, France

[73] Assignee: Roussel-UCLAF, Paris, France

[22] Filed: May 30, 1975

[21] Appl. No.: 582,270

Related U.S. Application Data

[63] Continuation-in-part of Ser. No. 398,415, Sept. 18, 1973, abandoned.

[30] Foreign Application Priority Data

Apr. 16, 1975 France .............................. 75.11784
Sept. 26, 1972 France .............................. 72.33960

[52] U.S. Cl. .............................. 71/118; 71/98; 71/103; 71/107; 260/558 S; 260/559 B; 260/559 R; 260/561 B; 260/562 R; 260/562 S
[51] Int. Cl.$^2$ ......... C07C 103/133; C07C 103/365; C07C 103/76
[58] Field of Search ....... 260/559 R, 559 B, 561 B, 260/562 S; 256/562 R; 71/98, 118

[56] References Cited

UNITED STATES PATENTS

| 2,781,345 | 2/1975 | Leavitt et al. | 260/288 |
| 3,556,768 | 1/1971 | Inoue et al. | 71/118 |
| 3,557,209 | 1/1971 | Richter et al. | 71/118 |
| 3,835,128 | 9/1974 | Bracha et al. | 260/559 R |
| 3,900,308 | 8/1975 | Poignant et al. | 71/118 |

OTHER PUBLICATIONS

Effenberger et al., Chem. Bericht 102 (1969), pp. 3260–3267.

*Primary Examiner*—Arthur P. Demers
*Attorney, Agent, or Firm*—Hammond & Littell

[57] ABSTRACT

Novel crotonanilides of the formula

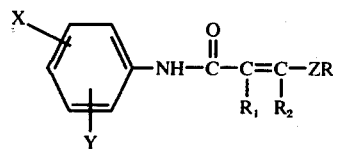

wherein Z is selected from the group consisting of —O— and —S—, R is selected from the group consisting of alkyl of 1 to 6 carbon atoms and optionally substituted phenyl, X and Y are individually selected from the group consisting of hydrogen, halogen, lower alkyl of 1 to 6 carbon atoms optionally substituted with at least one halogen, alkoxy of 1 to 3 carbon atoms, alkylthio and alkylsulfinyl of 1 to 6 carbon atoms, acyl of an organic carboxylic acid of 1 to 6 carbon atoms, —NO$_2$ and —CF$_3$, R$_1$ is selected from the group consisting of hydrogen, chlorine, bromine, alkoxycarbonyl with 1 to 6 alkyl carbon atoms, nitro and alkylthio, alkylsulfinyl and alkylsulfonyl of 1 to 3 alkyl carbon atoms and R$_2$ is alkyl of 1 to 6 carbon atoms, said compounds existing in the form of their E or Z isomers or mixtures thereof and having herbicidal properties.

17 Claims, No Drawings

NOVEL CROTONANILIDES

PRIOR APPLICATION

This application is a continuation-in-part of our co-pending, commonly assigned application Ser. No. 398,415 filed Sept. 18, 1973, now abandoned.

OBJECTS OF THE INVENTION

It is an object of the invention to provide the novel crotonanilides of formula I and a novel process for their preparation.

It is another object of the invention to provide novel herbicidal compositions.

It is a further object of the invention to provide a novel method of killing plants.

These and other objects and advantages of the invention will become obvious from the following detailed description.

THE INVENTION

The novel crotonanilides of the invention have the formula

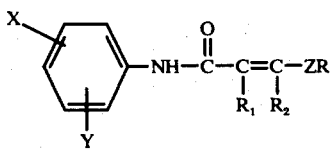

wherein Z is selected from the group consisting of —O— and —S—, R is selected from the group consisting of alkyl of 1 to 6 carbon atoms and optionally substituted phenyl, X and Y are individually selected from the group consisting of hydrogen, halogen, lower alkyl of 1 to 6 carbon atoms optionally substituted with at least one halogen, alkoxy of 1 to 3 carbon atoms, alkylthio and alkylsulfinyl of 1 to 6 carbon atoms, acyl of an organic carboxylic acid of 1 to 6 carbon atoms, preferably an alkanoic acid, —NO$_2$ and —CF$_3$, R$_1$ is selected from the group consisting of hydrogen, chlorine, bromine, alkoxycarbonyl with 1 to 6 alkyl carbon atoms, nitro and alkylthio, alkylsulfinyl and alkylsulfonyl of 1 to 3 alkyl carbon atoms and R$_2$ is alkyl of 1 to 6 carbon atoms, said compounds existing in the form of their E or Z isomers or mixtures thereof. The alkyl radicals are preferably methyl, ethyl, propyl or butyl.

The novel process of the invention for the preparation of the crotonanilides of formula I wherein R$_1$ is hydrogen and R$_2$ and R are alkyl of 1 to 6 carbon atoms comprises reacting a substituted anilide of the formula

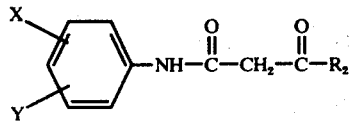

wherein X and Y have the above definition with either an O-alkylation agent to obtain the corresponding compound of formula I where Z is oxygen or with hydrogen sulfide in the presence of gaseous hydrogen chloride to obtain a compound of the formula

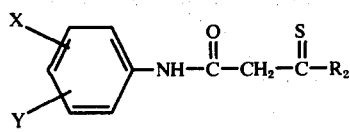

which is then treated with an S-alkylation agent to obtain the corresponding compound of formula I wherein Z is sulfur.

The O-alkylation agents may be alkyl orthoformates, alkyl halides or diazoalkanes but are preferably alkyl halides of the formula R-Hal where Hal is a halogen or alkyl orthoformates of the formula H—C(OR)$_3$. The reaction with alkyl orthoformates if preferably effected in the presence of an acid agent such as sulfuric acid. This reaction to compounds of formula I occurs in 2 steps: a first step of acetalization to obtain derivatives of the formula

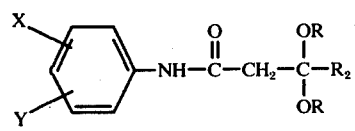

which are spontaneous transformed or transformed by heating to a compound of the formula

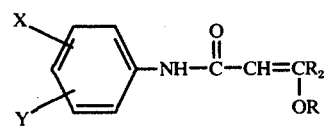

Generally, the use of alkyl orthoformates as the O-alkylation agent leads to the E isomers of the compounds of formula I while use of a diazoalkane leads to the Z isomers of the compounds of formula I.

The S-alkylation agents may be alkyl halides or diazoalkanes with the preferred agents being alkyl halides of the formula R-Hal where R is alkyl of 1 to 6 carbon atoms and Hal is a halogen.

The process of the invention for the preparation of compounds of formula I wherein R$_1$ is hydrogen, R$_2$ is methyl and R is as above comprises reacting β-chlorocrotonyl chloride with a substituted aniline of the formula

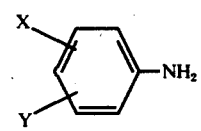

wherein X and Y have the above definition to obtain a compound of the formula

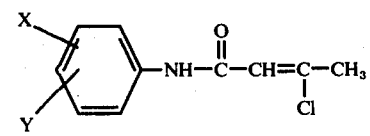

which can be treated with an alkali metal alkylate or arylate to obtain a compound of formula I wherein Z is oxygen or with an alkali metal thioalkylate or thioarylate to obtain the compound of formula I where Z is sulfur.

The process of the invention for the preparation of the products of formula I wherein $R_1$ is COOAkyl, —CN or nitro, $R_2$ is methyl and Z is oxygen and R is alkyl of 1 to 6 carbon atoms comprises reacting a compound of the formula

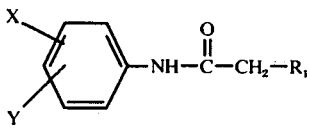   VI wherein X and Y have the above definition with an alkyl orthoacetate of the formula

   VII to obtain the corresponding compound of formula I.

The process of the invention for the preparation of compounds of formula I wherein $R_1$ is Cl, Br, alkylthio or alkylsulfinyl, $R_2$ is methyl, Z is oxygen and R is methyl comprises reacting a compound of the formula

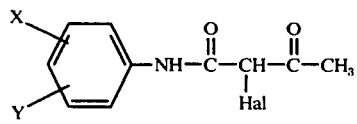   VIII wherein X and Y have the above definition and Hal is chlorine or bromine with either diazomethane to obtain the compound of formula I wherein $R_1$ is —Cl or —Br or with sodium or potassium thioalkylate to obtain a compound of the formula

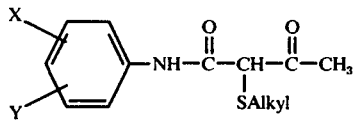   IX wherein alkyl has 1 to 3 carbon atoms which is reacted with methyl orthoformate to form the compound of formula I where $R_1$ is alkylthio which can be treated with an oxidation agent to form the corresponding alkylsulfinyl product.

The compounds of formula I where $R_1$ is alkylsulfonyl, $R_2$ is methyl, Z is oxygen and R is alkyl of 1 to 6 carbon atoms may be prepared by reacting an isocyanate of the formula

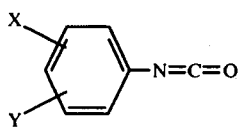   X wherein X and Y have the above definitions with an alkylsulfonylacetone of the formula

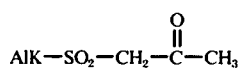   XI wherein Alk is alkyl of 1 to 3 carbon atoms to obtain a compound of the formula

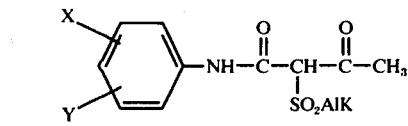   XII which is then reacted with an alkyl orthoformate to obtain the corresponding compound of formula I.

The various starting materials of the invention may be made by known processes. For example, the anilides of formula II can be prepared by reacting an alkyl acylacetate of the formula

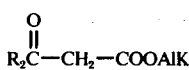

with a substituted aniline as described in J. Pharm. Soc. Japan, Vol. 69 (1949), p. 126. The anilide of formula VI can be prepared by reacting an aniline of formula IV with ethyl chlorocarbonylacetate, ethyl nitroacetate or ethyl cyanoacetate as described in J. Indian Chem. Soc., Vol. 4 (1927), p. 548. The anilides of formula VIII may be prepared from α-chloroacetoacetanilide is described in J. Indian Chem. Soc., Vol. 20 (1943), p. 384.

The novel herbicidal compositions of the invention contain as the active ingredient at least one compound of formula I with the optional presence of at least one other pesticidal agent or other products which influence the growth of plants. The said compositions possess both pre- and post-emergence herbicidal activity.

The compositions may be in the form of powders, granules, suspensions, emulsions or solutions containing, besides the active ingredients, cationic, anionic or non-ionic surface-active agents; inert powders such as talc, clays, silicates, Kieselguhr, etc.; a vehicle such as water, alcohols, hydrocarbon or other organic solvents, a mineral, animal or vegetable oil, etc.

An example of a useful herbicidal composition in the form of a wettable powder comprises 25% by weight of 3-methoxycrotonanilide or N-(m-tolyl)-3-methoxycrotonamide, 15% by weight of Ekapersol S (condensation product of sodium naphthalenesulfonate), 0.5% by weight of Brecolane NVA (sodium alkylnaphthalenesulfonate), 34.5% by weight of Zeosil 39 (precipitated synthetic hydrated silica) and 25% by weight of Vercoryl S (collodial kaolin). The compositions generally contain 10 to 80%, preferably 10 to 50%, by weight of the active ingredient.

The novel method of the invention for killing plants comprises contacting the plants with a herbicidally effective amount of at least one compound of formula I. The compounds may be applied to the soil before emergence of the plants or post-emergence to the growing plants above ground. The herbicidal amounts will vary depending upon the method of application and the particular products used.

In the following examples there are described several preferred embodiments to illustrate the invention. However, it should be understood that the invention is not intended to be limited to the specific embodiments.

EXAMPLE 1

N-(3', 4'-dichlorophenyl)-3-ethoxy-crotonamide

A mixture of 98.4 g of 3,4-dichloroacetoacetanilide and 6 drops of concentrated sulfuric acid in 60 g of ethyl orthoformate was stirred at 20° C for 3 hours and the mixture was then allowed to stand for 16 hours at 20° C. 12 drops of quinoline were added to the mixture which was then heated at 90° C under reduced pressure for 2 hours. Isopropyl ether was added thereto to obtain 40 g of N-(3',4'-dichlorophenyl)-3-ethoxy-crotonamide melting at 126° C after crystallization from methanol.

| Analysis: | $C_{12}H_{13}Cl_2NO_2$; | | | |
|---|---|---|---|---|
| Calculated: | %C 52.57 | %H 4.78 | %N 5.11 | %Cl 25.87 |
| Found: | 52.4 | 4.8 | 5.2 | 25.7 |

EXAMPLE 2

3-methoxy-crotonanilide

STEP A: N-phenyl-3,3-dimethoxybutyramide

A mixture of 43 g of methyl orthoformate and 5 drops of concentrated sulfuric acid in 70.8 g of acetoacetanilide was stirred at 20° C for 3 hours and the resulting solution stood for 20 hours at 20° C. The mixture was iced and the precipitate formed was recovered by vacuum filtration and was crystallized from isopropyl ether to obtain 54 g of N-phenyl-3,3-dimethoxybutyramide melting at 80° C.

| Analysis: | $C_{12}H_{17}NO_3$ | | |
|---|---|---|---|
| Calculated: | %C 64.57 | %H 7.62 | %N 6.28 |
| Found: | 64.3 | 7.3 | 6.4 |

STEP B: 3-methoxy-crotonanilide 558 g of N-phenyl-3,3-dimethoxybutyramide were heated for 1 hour at 195° C at a vacuum of 60 mm Hg and after cooling to 60° C, it was added to 500 ml of isopropyl ether. The mixture was cooled and vacuum filtered to obtain 226 g of 3-methoxy-crotonanilide in the form of white crystals melting at 111—112° C.

| Analysis: | $C_{11}H_{13}NO_2$ | | |
|---|---|---|---|
| Calculated: | %C 69.09 | %H 6.85 | %N 7.32 |
| Found: | 69.0 | 6.5 | 7.2 |

EXAMPLE 3

2-chloro-3-methoxy-crotonanilide 52.9 g of α-chloroacetoacetanilide in 500 ml of methylene chloride was held at 0° C for 4 hours and then 725 ml of methylene chloride solution titrating 17.4 g/l of diazomethane were added. The mixture was stirred for 16 hours at 0° C and then 1 hour at 20° C and was concentrated to dryness under reduced pressure. The residue was added to isopropyl ether and the precipitate formed was recovered by vacuum filtration and was crystallized from isopropyl ether to obtain 12 g of 2-chloro-3-methoxy-crotonanilide melting at 100° C.

| Analysis: | $C_{11}H_{12}ClNO_2$ | | | |
|---|---|---|---|---|
| Calculated: | %C 58.53 | %H 5.36 | %Cl 15.71 | %N 6.20 |
| Found: | 58.4 | 5.4 | 15.9 | 6.2 |

EXAMPLE 4

N-(3'-trifluoromethylphenyl)-3-methoxy-crotonamide

A mixture of 98 g of 3-trifluoromethylacetoacetanilide and 6 drops of concentrated sulfuric acid in 44 g of methyl orthoformate was stirred at 20° C for 3 hours and was then left standing at 20° C for 15 hours. 12 drops of quinoline and 500 ml of toluene were added thereto and the mixture was heated to 150° C for 1½ hours while distilling dropwise. The resulting toluene was distilled under reduced pressure and the residue was chromatographed over silica gel using a 8-2 methylene chloride-ethyl acetate mixture as eluant to obtain 55 g of N-(3'-trifluoromethylphenyl)-3-methoxy-crotonamide melting at 90° C.

| Analysis: | $C_{12}H_{12}F_3NO_2$ | | | |
|---|---|---|---|---|
| Calculated: | %C 55.60 | %H 4.67 | %F 21.99 | %N 5.40 |
| Found: | 55.4 | 4.7 | 21.8 | 5.1 |

EXAMPLE 5

N-(3', 4'-dichlorophenyl)-3-methoxy-crotonanilide (isomer Z)

450 ml of a methylene chloride solution titrating 2% of diazomethane were added with stirring to a mixture of 50 g of 3,4-dichloroacetoacetanilide in 200 ml of methylene chloride cooled to 0° C and the mixture was stirred for 3 hours at 0° C, then allowed to stand for 16 hours at room temperature. The methylene chloride was removed by distillation under reduced pressure and the residue is taken up in isopropyl ether. The solution was cooled and the precipitate formed was recovered by vacuum filtration to obtain 18 g of N-(3', 4'-dichlorophenyl)-3-methoxy-crotonamide which melted at 123° C after crystallization from isopropyl ether.

| Analysis: | $C_{11}H_{11}Cl_2NO_2$ | | | |
|---|---|---|---|---|
| Calculated: | %C 50.79 | %H 4.26 | %Cl 27.26 | %N 5.39 |
| Found: | 50.8 | 4.3 | 27.0 | 5.5 |

EXAMPLE 6

N-(3',4'-dichlorophenyl)-3-methoxy-crotonamide (isomer E)

A mixture of 98 g of 3,4-dichloroacetoacetanilide, 6 drops of concentrated sulfuric acid and 44 g methyl orthoformate was stirred for 3 hours and then allowed to stand at 20° C for 16 hours. After cooling, the resulting precipitate was recovered by vacuum filtration to obtain 40 g of N-(3', ,4'-dichlorophenyl)-3-methoxy-crotonamide melting at 156° C after crystallization from methanol.

| Analysis:   | C₁₁H₁₁Cl₂NO₂ |         |          |         |
|-------------|--------------|---------|----------|---------|
| Calculated: | %C 50.79     | %H 4.26 | %Cl 27.26| %N 5.39 |
| Found:      | 50.9         | 4.2     | 26.8     | 5.4     |

EXAMPLE 7

N-(o-tolyl)-3-methoxy-crotonamide

A mixture of 80 g of trimethyl orthoformate, 110 g of O-methyl-acetoacetanilide and 6 drops of concentrated sulfuric acid was stirred for 8 hours and was then allowed to stand at 20° C for 16 hours. 12 drops of quinoline were added to the mixture which was then filtered to remove insolubles. The filtrate was evaporated to dryness by distilliation under reduced pressure and the residue was added to xylene. The mixture was refluxed for 5 hours and the xylene was concentrated by distillation under reduced pressure. Isopropyl ether was added and the precipitate formed was recovered by vacuum filtration. The product was purified by chromatography over silica gel with a 8-2 methylene chloride-ethyl acetate mixture as eluant to obtain 30 g of N-(o-tolyl)-3-methoxy-crotonamide melting at 101° C.

| Analysis:   | C₁₂H₁₅NO₂ |         |         |
|-------------|-----------|---------|---------|
| Calculated: | %C 70.23  | %H 7.36 | %N 6.82 |
| Found:      | 70.2      | 7.6     | 6.9     |

EXAMPLE 8

3-methoxy-2-hexenanilide

STEP A: 3,3-dimethoxy-hexananilide 10 drops of concentrated sulfuric acid and 68 g of butyryl acetanilide in 80 g of methyl orthoformate was stirred for 3 hours and then allowed to stand for 16 hours. After cooling, the precipitate formed was recovered by vacuum filtration, was washed and dried to obtain 66 g of 3,3-dimethoxy-hexananilide melting at 88° C.

STEP B: 3-methoxy-2-hexenanilide 60 g of 3,3-dimethoxy-hexananilide were heated at 145° C until the distillation of methanol ceased and after cooling, isopropyl ether was added thereto. The precipitate formed was recovered by vacuum filtration to obtain 24 g of 3-methoxy-2-hexenanilide melting at 104° C.

| Analysis:   | C₁₃H₁₇NO₂ |         |         |
|-------------|-----------|---------|---------|
| Calculated: | %C 71.19  | %H 7.82 | %N 6.39 |
| Found:      | 71.4      | 7.9     | 6.4     |

EXAMPLE 9

3-methylthio-crotonanilide

STEP A: Thioacetoacetanilide

A current of hydrochloric gas was bubbled through 500 ml of ethanol cooled to −30° C until saturation was reached and hydrogen sulfide was bubbled therethrough for 30 minutes at −10° C. Then, 35.5 g of acetoacetanilide were added thereto and hydrogen sulfide was bubbled therethrough at 0° C for 16 hours with stirring. The mixture was concentrated to dryness under reduced pressure and the residue was chromatographed over silica gel and the eluant was a 1—1 mixture of acetone and chloroform to obtain 13 g of thioacetoacetanilide melting at 125° C.

STEP B: 3-methylthio-crotonanilide 11.6 g of thioacetoacetanilide and then a solution of 3.4 g of potassium hydroxide in 35 ml of ethanol were added to 60 ml of ethanol and the mixture was stirred for an hour at 20° C. 8.5 g of methyl iodide were added thereto and the mixture was poured into 300 ml of water. The precipitate formed was recovered by vacuum filtration, and was dissolved in chloroform. The chloroform solution was dried and concentrated to dryness under reduced pressure to obtain 12g of 3-methylthio-crotonanilide melting at 175° C. After crystallization from acetone, the melting point was 178° C.

| Analysis:   | C₁₁H₁₃NOS |         |         |          |
|-------------|-----------|---------|---------|----------|
| Calculated: | %C 63.73  | %H 6.32 | %N 6.75 | %S 15.47 |
| Found:      | 63.5      | 6.1     | 6.7     | 15.5     |

EXAMPLE 10

N-(m-tolyl)-3-methoxy-crotonamide

A mixture of 80 g of N-(m-tolyl)-acetoacetamide, 80 g of methyl orthoformate, 100 ml of methanol and 1 g of p-toluene sulfonic acid was refluxed with stirring for 6 hours and the volatile material was distilled off under reduced pressure. 300 ml of toluene and 1.5 ml of quinoline were added and the mixture was heated to about 140° C for 3 hours and then the rest of the toluene was evaporated. The residue was chromatographed over silica gel with a mixture of 9-1 methylene chloride-ethyl acetate as eluant to obtain 40 g of N-(m-tolyl)-3-methoxy-crotonamide melting at 106° C.

| Analysis:   | C₁₂H₁₅NO₂ |         |         |
|-------------|-----------|---------|---------|
| Calculated: | %C 70.23  | %H 7.37 | %N 6.82 |
| Found:      | 70.4      | 7.3     | 6.6     |

EXAMPLE 11

Using the procedure of Example 10, the crotonamides of Table I were prepared.

TABLE I

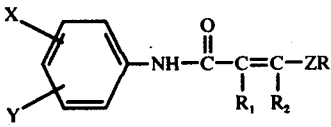

| X | Y | Z | R | R₁ | R₂ | Melting point in °C |
|---|---|---|---|---|---|---|
| 2-CH$_3$ | 6-CH$_3$ | O | CH$_3$ | H | CH$_3$ | 163 |
| 4-NO$_2$ | H | O | CH$_3$ | H | CH$_3$ | 180 |
| 3-Cl | 4-CH$_3$ | O | CH$_3$ | H | CH$_3$ | 118 |
| 3-Cl | 5-Cl | O | CH$_3$ | H | CH$_3$ | 139 |
| 3-Cl | 4-OCH$_3$ | O | CH$_3$ | H | CH$_3$ | 136 |
| 3-NO$_2$ | H | O | CH$_3$ | H | CH$_3$ | 187 |
| 3-SOCH$_3$ | H | O | CH$_3$ | H | CH$_3$ | 157 |
| H | H | O | CH$_2$—CH$_2$—CH$_3$ | H | CH$_3$ | 75 |
| H | H | O | CH$_2$—CH$_2$—CH$_2$—CH$_3$ | H | CH$_3$ | 102 |
| 4-OCH$_3$ | H | O | CH$_3$ | H | CH$_3$ | 104 |
| 4-CH$_3$ | H | O | CH$_3$ | H | CH$_3$ | 109 |
| 2-Cl | H | O | CH$_3$ | H | CH$_3$ | 72 |
| H | H | O | CH$_2$—CH$_3$ | H | CH$_3$ | 118 |
| 4-Br | H | O | CH$_3$ | H | CH$_3$ | 152 |
| 4-Cl | H | O | CH$_3$ | H | CH$_3$ | 124 |
| 3-Cl | H | O | CH$_3$ | H | CH$_3$ | 104 |
| 2-CH$_3$ | 5-Cl | O | CH$_3$ | H | CH$_3$ | 150 |
| 2-CH$_3$ | 4-Cl | O | CH$_3$ | H | CH$_3$ | 157 |
| 2-OCH$_3$ | 5-Cl | O | CH$_3$ | H | CH$_3$ | 134 |
| 3-O—CH$_2$—CH$_2$C(CH$_3$)(CH$_3$)—CH$_3$ | H | O | CH$_3$ | H | CH$_3$ | 94 |

EXAMPLE 12

3-methoxy-2-methylthio-crotonanilide 2-methylthioacetoacetanilide [formed from α-chloroacetoacetanilide and sodium methylmercaptan] was reacted with diazomethane to obtain 3-methoxy-2-methylthio-crotonanilide melting at 155° C.

EXAMPLE 13

3-phenoxy-crotonanilide 3-methoxy-crotonanilide [formed from aniline and β-chloro-crotonyl chloride] was reacted with phenol in a basic media to obtain 3-phenoxy-crotonanilide melting at 145° C.

EXAMPLE 14 m-methylthio-3-methoxy-crotonanilide

STEP A: m-methylthio-acetylacetanilide 84 g of diketene were added over 30 minutes to a mixture of 139 g of m-thioanisidine in 500 ml of benzene and the mixture was stirred at 20° C for 5 hours. The benzene was then distilled under reduced pressure and the oil residue was taken up in 200 ml of isopropyl ether. After cooling, the mixture was vacuum filtered. The recovered crystals were dried to obtain 185 g of m-methylthio-acetylacetanilide melting at 67° to 68° C.

STEP B: m-methylthio-3-methoxy-crotonanilide

A mixture of 67 g of m-methylthio-acetylacetanilide, 46.8 g of methyl orthoformate, 100 ml of methanol and 1 g of p-toluene sulfonic acid was stirred for 3 hours at 20° C and after cooling to 0° C, the mixture was vacuum filtered. The resulting crystals melting at 91° C were added to 200 ml of toluene and the mixture was heated at 140° C for 3 hours while distilling the azeotrope formed. Then, the rest of the toluene was evaporated and the residue was chromatographed over silica gel. Elution with an 8-2 mixture of methylene chloride and ethyl acetate yielded 40 g m-methylthio-3-methoxycrotonanilide melting at 70-71° C.

| Analysis: | C$_{12}$H$_{15}$NO$_2$S | | | |
|---|---|---|---|---|
| Calculated: | %C 60.73 | %H 6.37 | %N 5.90 | %S 13.52 |
| Found: | 60.8 | 6.5 | 5.7 | 13.5 |

EXAMPLE 15 m-(n-butyl)-3-methoxy-crotonanilide

STEP A: m-(n-butyl)-acetylacetanilide 3.9 g of diketene were added to a mixture of 6.9 g of m-(n-butyl)-aniline and 70 ml of benzene and the mixture was stirred for 2 hours at 30° C. The benzene was evaporated under reduced pressure and the residue was chromatographed over silica gel. Elution with an 8-2 mixture of methylene chloride and ethyl acetate yielded 8.5 g of m-(n-butyl)-acetylacetanilide in the form of an oil with a refractive index of n$_D$20 = 1.5355.

STEP B: m-(n-butyl)-3-methoxy-crotonanilide

A mixture of 8.5 g of m-(n-butyl)-acetylacetanilide, 5.7 g of methyl orthoformate, 80 ml of methanol and 0.3 g of p-toluene sulfonic acid was stirred at 20° C for 16 hours and after the addition of 100 ml of toluene and 0.6 ml of quinoline, the mixture was heated at 140° C for one hour while distilling the toluene-methanol azeotrope. After refluxing for 30 minutes, another 100 ml of toluene were added thereto and the reaction was completed when the solvent was evaporated. The residue was chromatographed over silica gel and elution with an 8-2 mixture was methylene chloride and ethyl acetate yielded 6.3 g of m-(n-butyl)-3-methoxy-crotonanilide melting at 36° C.

| Analysis: | C$_{15}$H$_{21}$NO$_2$ | | |
|---|---|---|---|
| Calculated: | %C 72.83 | %H 8.55 | %N 5.66 |
| Found: | 73.0 | 8.7 | 5.7 |

EXAMPLE 16 m-butyryl-3-methoxy-crotonanilide

STEP A: n-butyryl-3-chlorocrotonanilide 29.2 g of β-chlorocrotonyl chloride were added over one hour at 0° C to a mixture of 31 g of m-aminobutyrophenone 21.2 g of triethylamine and 300 ml of tetrahydrofuran and after stirring for 16 hours at 20° C, the mixture was vacuum filtered. The filtrate was concentrated to dryness and the residue was chromatographed over silica gel to obtain 25 g of m-butyryl-3-chlorocrotonanilide melting at 106° C.

STEP B: m-butyryl-3-methoxy-crotonanilide 5.4 g of sodium methylate were added with stirring to a mixture of 26.5 g of m-butyryl-3-chlorocrotonanilide and 250 ml of methanol and after stirring for 4 hours at 20° C, the mixture was vacuum filtered to remove sodium chloride. The filtrate was concentrated to dryness under reduced pressure and the residue was chromatographed over silica gel. Elution with a 7-3 mixture of benzene and ethyl acetate yielded 14 g of m-butyryl-3-methoxy-crotonanilide melting at 81° C.

| Analysis: | $C_{15}H_{19}NO_3$ | | |
|---|---|---|---|
| Calculated: | %C 68.94 | %H 7.32 | %N 5.36 |
| Found: | 68.9 | 7.6 | 5.3 |

EXAMPLE 17 m-acetyl-3-methoxy-crotonanilide

STEP A: m-acetyl-3-chlorocrotonanilide 15.2 g of β-chlorocrotonyl chloride were added over 10 minutes to a mixture of 13.5 g of 3-amino-acetophenone, 11.1 g of triethylamine and 130 ml of tetrahydrofuran and after stirring for one hour at 0° C, the mixture was filtered. The filtrate was washed with 100 ml of tetrahydrofuran and the filtrate was evaporated to dryness and the residue was chromatographed over silica gel. Elution with a 7-3 benzene-ethyl acetate mixture yielded 10 g of m-acetyl-3-chlorocroton anilide melting at 152° C.

STEP B: m-acetyl-3-methoxy-crotonanilide

A mixture of 400 ml of methanol, 41 g of m-acetyl-3-chlorocrotonanilide and 9.4 g of sodium methylate was stirred at 20° C for 72 hours and the mixture was vacuum filtered to recover the sodium chloride formed and the desired product. The solid was dissolved in refluxing acetone and the mixture was filtered. The filtrate was evaporated to dryness under reduced pressure. The waste were evaporated to dryness and the residue was taken up in 200 ml of a 7-3 benzene-ethyl acetate mixture. The mixture was vacuum filtered and the solid was dissolved in refluxing acetone. The solution was filtered and the filtrate was evaporated to dryness for a total yield of 19.5 g of m-acetyl-3-methoxy-crotonanilide melting at 168° C.

| Analysis: | $C_{13}H_{15}NO_3$ | | |
|---|---|---|---|
| Calculated: | %C 66.93 | %H 6.48 | %N 6.00 |
| Found: | 67.1 | 6.5 | 5.7 |

EXAMPLE 18 m-bromo-3-methoxy-crotonanilide

STEP A: m-bromo-acetylacetanilide 84 g of diketene were added over 20 minutes to a mixture of 172 g of m-bromo-aniline and 600 ml of benzene and the mixture was stirred for 5 hours at 20° C. The mixture was filtered and the precipitate was washed with benzene and isopropyl ether. The filtrate was vacuum filtered and evaporated to dryness to obtain 189 g of m-bromo-acetylacetanilide melting at 110° C.

STEP B: m-bromo-3-methoxy-crotonanilide

A mixture of 68.5 g of m-bromo-acetylacetanilide, 39.6 g of methyl orthoformate, 160 ml of methanol and 0.5 g of p-toluene sulfonic acid was stirred for 2 hours at 20° C and after the addition of 1 ml of quinoline, the mixture was evaporated to dryness under reduced pressure. The 83 g of colorless oil residue was taken up in 400 ml of toluene and the mixture was heated at 140° C for 4 hours while distilling the toluene-methanol azeotrope formed. After cooling, the toluene was evaporated under reduced pressure and the residue was chromatographed over silica gel. The product was eluted with a 9-1 mixture of methylene chloride and ethyl acetate and the fraction with an Rf = 0.65 was taken up in isopropyl ether to obtain 44 g of m-bromo-3-methoxy-crotonanilide melting at 110° C.

| Analysis: | $C_{11}H_{12}BrNO_2$ | | | |
|---|---|---|---|---|
| Calculated: | %C 48.91 | %H 4.47 | %N 5.18 | %Br 29.59 |
| Found: | 49.1 | 4.4 | 5.10 | 29.5 |

PRE-AND POST EMERGENCE HERBICIDAL ACTIVITY

The test plants were bent grass, oats, wheat, corn, rye grass, vulpin, barley, beets, chenopode, chrysanthemum, mustard, rumex, clover and gaillet. The plants were cultivated in a culture box (23×14×4 cm) with a double bottom and with watering from below. The seeds were placed in rows spaced 3 cm apart using 20 seeds per species in a single box using 4 boxes for each concentration. The growing conditions were as follows: temperature of 20° C + 2° C, humidity about 60% and illumination with fluorescent lights (day light & white light) 6 to 22 hours per day. The dirt mixture used is 10 volumes of pure dirt, 10 volumes of river sand and 2 volumes of peat.

In the pre-emergence test, treatment was effected 24 hours after the sowing and the first wetting was effected by aspersion so as to carry a part of the product to the level of the seeds. For the post-emergence test, the treatment was effected after 21 days of growing with above ground growth. In both cases, the test product was applied under standard conditions with a microsprayer at the indicated dose at a dilution equal to 560 l/ha. The tests included controls without treatment and as comparative standards Metoxuron or (N,N-dimethyl-N'-3-chloro-4-methoxyphenyl)-urea, Linuron or N-(3,4-dichlorophenyl)-N'-methoxy-N'-methyl-urea, Nitrofene or (2,4-dichlorophenyl)-4'-nitrophenyl-ether and Metabenzthiazuron or [1-methyl-3-(2-benzothiazolyl)-urea]. The final readings were effected by the weight of the plants 21 days after pre-emergence treatment and 15 days after post-emergence treatment.

The results are expressed as a percent of reduction of vegetation P:

$$P = \frac{\text{weight of control plants} - \text{weight of treated plants}}{\text{weight of control plants}} \times 100$$

Tables 1 and 2 show the results with 3-methoxy-crotonanilide (compound A) and Tables 3 and 4 show the results with N-(m-tolyl)-3-methoxy-crotonamide (compound B). Tables 5 to 12 show the results obtained with m-methylthio-3-methoxy-crotananilide (compound C), m-(n-butyl)-3-methoxy-crotonanilide (compound D), m-butyryl-3-methoxy-crotonanilide (compound E), m-acetyl-3-methoxy-crotonanilide (compound F) and m-bromo-3-methoxy-crotonanilide (compound G).

TABLE 1

| | Dose kg/ha | Bent grass | Oats | Wheat | Corn | Barley | pre-emergence Rye grass | Vulpin | Beets | Cheno-podie | Chrysan-themum | Gaillet | Mus-tard | Rumex | Clover |
|---|---|---|---|---|---|---|---|---|---|---|---|---|---|---|---|
| Compound A | 0.625 | 100 | 83 | 58 | 0 | 41 | 100 | 100 | 100 | 100 | 100 | 45 | 100 | 100 | 100 |
| | 0.312 | 100 | 43 | 20 | 0 | 0 | 100 | 80 | 100 | 100 | 100 | 0 | 100 | 100 | 100 |
| | 0.156 | 100 | 25 | 0 | 0 | 0 | 100 | 82 | 95 | 100 | 63 | 0 | 100 | 100 | 100 |
| Nitrofene | 0.625 | 90 | 72 | 0 | 0 | 34 | 25 | 43 | | | | | | | |
| | 0.312 | 60 | 0 | 0 | 0 | 0 | 0 | 0 | | | | | | | |
| | 0.156 | 0 | 0 | 0 | 0 | 0 | 0 | 0 | | | | | | | |
| Metabenz-thiazuron | 0.625 | | | | | | | | 89 | 100 | 100 | 33 | 100 | 100 | 100 |
| | 0.312 | | | | | | | | 35 | 97 | 100 | 35 | 100 | 100 | 100 |
| | 0.156 | | | | | | | | 0 | 48 | 94 | 36 | 92 | 90 | 87 |

TABLE 2

| | Dose kg/ha | Bent grass | Oats | Wheat | Corn | Barley | post-emergence Rye Grass | Vulpin | Beets | Cheno-podie | Chrysan-themum | Gaillet | Mus-tard | Rumex | Clover |
|---|---|---|---|---|---|---|---|---|---|---|---|---|---|---|---|
| Compound A | 0.625 | 100 | 92 | 34 | 0 | 62 | 100 | 100 | 100 | 100 | 100 | 0 | 100 | 88 | 100 |
| | 0.312 | 100 | 54 | 0 | 0 | 0 | 82 | 57 | 98 | 100 | 100 | 0 | 57 | 64 | 100 |
| | 0.156 | 100 | 0 | 0 | 0 | 36 | 50 | 36 | 85 | 100 | 86 | 0 | 0 | 30 | 94 |
| Metoxuron | 0.625 | 82 | 0 | 0 | 41 | 0 | 52 | 68 | | | | | | | |
| | 0.312 | 70 | 0 | 0 | 0 | 0 | 0 | 0 | | | | | | | |
| | 0.156 | 44 | 0 | 0 | 0 | 0 | 0 | 0 | | | | | | | |
| Linuron | 0.625 | | | | | | | | 100 | 100 | 100 | 45 | 100 | 100 | 100 |
| | 0.312 | | | | | | | | 100 | 100 | 100 | 0 | 100 | 100 | 100 |
| | 0.156 | | | | | | | | 80 | 100 | 70 | 0 | 96 | 79 | 91 |

TABLE 3

| | Dose kg/ha | Bent grass | Oats | Wheat | Corn | Barley | Pre-emergence Rye Grass | Vul-pin | Beets | Cheno-podie | Chrysan-themum | Gaillet | Mus-tard | Rumex | Clover |
|---|---|---|---|---|---|---|---|---|---|---|---|---|---|---|---|
| Compound B | 5 | 100 | 0 | 59 | 0 | 100 | 100 | 83 | 100 | 100 | 100 | 100 | 100 | 100 | 100 |
| | 2.5 | 100 | 0 | 47 | 0 | 100 | 100 | 67 | 100 | 100 | 100 | 100 | 100 | 100 | 100 |
| | 1.25 | 78 | 0 | 0 | 0 | 100 | 100 | 81 | 100 | 100 | 34 | 100 | 100 | 100 | 100 |
| | 0.625 | 51 | 0 | 0 | 0 | 100 | 86 | 69 | 40 | 10 | 0 | 72 | 88 | 36 | 100 |
| NITROFENE | 5 | 69 | 25 | 0 | 0 | 100 | 59 | 100 | | | | | | | |
| | 2.5 | 31 | 0 | 0 | 0 | 100 | 68 | 57 | | | | | | | |
| | 1.25 | 31 | 0 | 0 | 0 | 100 | 47 | 45 | | | | | | | |
| | 0.625 | 24 | 0 | 0 | 0 | 60 | 0 | 51 | | | | | | | |
| METABENZ-THIAZURON | 5 | | | | | | | | 100 | 100 | 100 | 100 | 100 | 100 | 100 |
| | 2.5 | | | | | | | | 100 | 100 | 100 | 100 | 100 | 100 | 100 |
| | 1.25 | | | | | | | | 100 | 100 | 100 | 100 | 100 | 100 | 100 |
| | 0.625 | | | | | | | | 100 | 100 | 100 | 100 | 100 | 100 | 100 |

TABLE 4

| | Dose kg/ha | Oats | Wheat | Barley | Corn | Bent grass | Post-emergence Rye grass | Vul-pin | Beets | Cheno-podie | Chrysan-themum | Gaillet | Mus-tard | Rumex | Clover |
|---|---|---|---|---|---|---|---|---|---|---|---|---|---|---|---|
| Compound B | 5 | 100 | 100 | 100 | 100 | 100 | 100 | 100 | 100 | 100 | 100 | — | 100 | 100 | 100 |
| | 2.5 | 100 | 100 | 100 | 100 | 100 | 100 | 100 | 100 | 100 | 100 | — | 100 | 100 | 100 |
| | 1.25 | 100 | 75 | 100 | 45 | 100 | 100 | 100 | 100 | 100 | 100 | — | 100 | 100 | 100 |
| | 0.625 | 92 | 0 | 53 | 0 | 100 | 100 | 36 | 100 | 100 | 100 | — | 100 | 100 | 100 |
| METO-XURON | 5 | 100 | 0 | 60 | 71 | 100 | 100 | 100 | | | | | | | |
| | 2.5 | 46 | 0 | 0 | 0 | 100 | 100 | 80 | | | | | | | |
| | 1.25 | 29 | 0 | 0 | 0 | 70 | 20 | 0 | | | | | | | |
| | 0.625 | 0 | 0 | 0 | 0 | 0 | 36 | 0 | | | | | | | |
| LINURON | 5 | | | | | | | | 100 | 100 | 100 | 100 | 100 | 100 | 100 |
| | 2.5 | | | | | | | | 100 | 100 | 100 | 100 | 100 | 100 | 100 |
| | 1.25 | | | | | | | | 100 | 100 | 100 | 100 | 100 | 100 | 100 |
| | 0.625 | | | | | | | | 100 | 100 | 100 | 100 | 100 | 100 | 100 |

TABLE 5

| POST-EMERGENCE | | | | |
|---|---|---|---|---|
| Concentration in kg/ha of product C | 5.0 | 2.5 | 1.25 | 0.625 |
| Wheat | 0 | 0 | 0 | 0 |
| Barley | 23 | 0 | 0 | 0 |
| Corn | 53 | 25 | 0 | 0 |
| Oats | 0 | 0 | 0 | 0 |
| Bent Grass | 90 | 65 | 53 | 0 |
| Rye-Grass | 51 | 0 | 0 | 0 |
| Vulpin | 100 | 68 | 21 | 25 |
| Beets | 100 | 100 | 100 | 100 |
| Chenopodium | 100 | 100 | 100 | 100 |
| Chrysanthemum | 100 | 100 | 92 | 62 |
| Mustard | 100 | 100 | 100 | 100 |
| Rumex | 100 | 100 | 91 | 97 |
| Clover | 100 | 100 | 84 | 88 |
| Gaillet | 100 | 100 | 94 | 76 |

TABLE 6

| PRE-EMERGENCE | | | | |
|---|---|---|---|---|
| Concentration in kg/ha of product D | 5.0 | 2.5 | 1.25 | 0.625 |
| Wheat | 0 | 0 | 0 | 0 |
| Barley | 0 | 0 | 0 | 0 |
| Corn | 0 | 0 | 0 | 0 |
| Oats | 0 | 0 | 0 | 0 |
| Bent Grass | 0 | 0 | 0 | 0 |
| Rye-Grass | 0 | 0 | 0 | 0 |
| Vulpin | 0 | 0 | 0 | 0 |
| Beets | 94 | 85 | 0 | 0 |
| Chenopodium | 100 | 100 | 67 | 0 |
| Chrysanthemum | 78 | 58 | 0 | 0 |
| Mustard | 100 | 100 | 86 | 29 |
| Rumex | 100 | 91 | 0 | 0 |
| Clover | 100 | 100 | 0 | 0 |

TABLE 7

| POST-EMERGENCE | | | | |
|---|---|---|---|---|
| Concentration in kg/ha of product D | 5.0 | 2.5 | 1.25 | 0.625 |
| Wheat | 100 | 100 | 56 | 53 |
| Barley | 100 | 100 | 50 | 35 |
| Corn | — | 45 | 0 | 0 |
| Oats | 100 | 100 | 0 | 0 |
| Bent Grass | 100 | 100 | 100 | 100 |
| Rye-Grass | 100 | 100 | 100 | 100 |
| Vulpin | 100 | 85 | 54 | 31 |
| Beets | 100 | 100 | 100 | 100 |
| Chenopodium | 100 | 100 | 100 | 100 |
| Chrysanthemum | 100 | 100 | 100 | 100 |
| Mustard | 100 | 100 | 100 | 100 |
| Rumex | 100 | 100 | 100 | 100 |
| Clover | 100 | 100 | 100 | 100 |

TABLE 8

| PRE-EMERGENCE | | | | |
|---|---|---|---|---|
| Concentration in kg/ha of product E | 5.0 | 2.5 | 1.25 | 0.625 |
| Wheat | 0 | 0 | 0 | 0 |
| Barley | 0 | 0 | 0 | 0 |
| Corn | 0 | 0 | 0 | 0 |
| Oats | 0 | 0 | 0 | 0 |
| Bent Grass | 0 | 0 | 0 | 0 |
| Rye-Grass | 0 | 0 | 0 | 0 |
| Vulpin | 0 | 0 | 0 | 0 |
| Beets | 85 | 91 | 47 | 0 |
| Chenopodium | 67 | 0 | 0 | 0 |
| Chrysanthemum | 100 | 90 | 46 | 0 |
| Mustard | 100 | 86 | 57 | 0 |
| Rumex | 100 | 89 | 43 | 0 |
| Clover | 73 | 62 | 0 | 0 |
| Gaillet | 0 | 0 | 0 | 0 |

TABLE 9

| POST-EMERGENCE | | | | |
|---|---|---|---|---|
| Concentration in kg/ha of product E | 5.0 | 2.5 | 1.25 | 0.625 |
| Wheat | 82 | 60 | 0 | 0 |
| Barley | 73 | 89 | 0 | 0 |
| Corn | 84 | 74 | 0 | 0 |
| Oats | 42 | 0 | 0 | 0 |
| Bent Grass | 100 | 100 | 0 | 0 |
| Rye-Grass | 66 | 71 | 0 | 0 |
| Vulpin | 63 | 42 | 0 | 0 |
| Beets | 100 | 100 | 100 | 100 |
| Chenopodium | 100 | 100 | 100 | 100 |
| Chrysanthemum | 100 | 100 | 100 | 100 |
| Mustard | 100 | 100 | 100 | 100 |
| Rumex | 100 | 100 | 100 | 100 |
| Clover | 100 | 100 | 100 | 100 |
| Gaillet | 100 | 100 | 100 | 100 |

TABLE 10

| PRE-EMERGENCE | | | | |
|---|---|---|---|---|
| Concentration in kg/ha of product F | 5.0 | 2.5 | 1.25 | 0.625 |
| Wheat | 0 | 0 | 0 | 0 |
| Barley | 0 | 0 | 0 | 0 |
| Corn | 0 | 0 | 0 | 0 |
| Oats | 0 | 0 | 0 | 0 |
| Bent Grass | 71 | 0 | 0 | 0 |
| Rye-Grass | 28 | 0 | 0 | 0 |
| Vulpin | 31 | 0 | 0 | 0 |
| Beets | 0 | 0 | 0 | 0 |
| Chenopodium | 0 | 0 | 0 | 0 |
| Chrysanthemum | 100 | 100 | 72 | 36 |
| Mustard | 100 | 86 | 71 | 29 |
| Rumex | 29 | 0 | 0 | 0 |
| Clover | 46 | 0 | 0 | 0 |
| Gaillet | 0 | 0 | 0 | 0 |

TABLE 11

| PRE-EMERGENCE | | | | |
|---|---|---|---|---|
| Concentration in kg/ha of product G | 5.0 | 2.5 | 1.25 | 0.625 |
| Wheat | 0 | 0 | 0 | 0 |
| Barley | 61 | 0 | 0 | 0 |
| Corn | 0 | 0 | 0 | 0 |
| Oats | 59 | 74 | 0 | 0 |
| Bent Grass | 49 | 0 | 0 | 0 |
| Rye-Grass | 100 | 100 | 77 | 27 |
| Vulpin | 100 | 0 | 0 | 0 |
| Beets | 100 | 100 | 100 | 28 |
| Chenopodium | 100 | 100 | 61 | 23 |
| Chrysanthemum | 100 | 100 | 57 | 0 |
| Mustard | 100 | 100 | 95 | 0 |
| Rumex | 100 | 100 | 100 | 36 |
| Clover | 100 | 100 | 100 | 100 |
| Gaillet | 72 | 28 | 0 | 0 |

TABLE 12

| POST-EMERGENCE | | | | |
|---|---|---|---|---|
| Concentration in kg/ha of product G | 5.0 | 2.5 | 1.25 | 0.625 |
| Wheat | 100 | 100 | 47 | 0 |
| Barley | 100 | 100 | 80 | 39 |
| Corn | 100 | 100 | 35 | 37 |
| Oats | 100 | 100 | 71 | 30 |
| Bent Grass | 100 | 100 | 100 | 100 |
| Rye-Grass | 100 | 100 | 100 | 100 |
| Vulpin | 100 | 100 | 75 | 0 |
| Beets | 100 | 100 | 100 | 100 |
| Chenopodium | 100 | 100 | 100 | 100 |
| Chrysanthemum | 100 | 100 | 100 | 100 |
| Mustard | 100 | 100 | 100 | 100 |
| Rumex | 100 | 100 | 100 | 100 |
| Clover | 100 | 100 | 100 | 100 |
| Gaillet | 100 | 100 | 100 | 100 |

Tables 1 to 12 show that 3-methoxy-crotonanilide and N-(m-tolyl)-3-methoxy-crotonamide and the other tested products possess interesting pre- and post-emergence herbicidal activity.

Various modifications of the products and methods of the invention may be made without departing from the spirit or scope thereof and it should be understood that the invention is to be limited only as defined in the appended claims.

We claim:

1. A crotonanilide of the formula

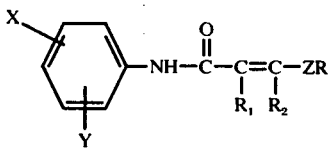

wherein Z is selected from the group consisting of —O— and —S—, R is selected from the group consisting of alkyl of 1 to 6 carbon atoms and phenyl, X and Y are individually selected from the group consisting of hydrogen, halogen, lower alkyl of 1 to 6 carbon atoms optionally substituted with at least one halogen, alkoxy of 1 to 3 carbon atoms, alkylthio and alkylsulfinyl of 1 to 6 carbon atoms, acyl of an organic carboxylic acid of 1 to 6 carbon atoms, —NO$_2$ and —CF$_3$, R$_1$ is selected from the group consisting of hydrogen, chloride, bromine, alkoxycarbonyl with 1 to 6 alkyl carbon atoms, nitro and alkylthio, alkylsulfinyl and alkylsulfonyl of 1 to 3 alkyl carbon atoms and R$_2$ is alkyl of 1 to 6 carbon atoms, said compounds existing in the form of their E or Z isomers or mixtures thereof.

2. A compound of claim 1 which is 3-methoxy-crotonanilide.

3. A compound of claim 1 which is N-(m-trifluoromethylphenyl)-3-methoxy-crotonamide.

4. A compound of claim 1 which is N-(o-tolyl)-3-methoxy-crotonamide.

5. A compound of claim 1 which is N-(m-tolyl)-3-methoxy-crotonamide.

6. A compound of claim 1 which is N-(3'-chlorophenyl)-3-methoxy-crotonamide.

7. A compound of claim 1 which is m-methylthio-3-methoxy-crotonanilide.

8. A compound of claim 1 which is m-(n-butyl)-3-methoxy-crotonanilide.

9. A compound of claim 1 which is m-butyryl-3-methoxy-crotonanilide.

10. A compound of claim 1 which is m-acetyl-3-methoxy-crotonanilide.

11. A compound of claim 1 which is m-bromo-3-methoxy-crotonanilide.

12. A herbicidal composition comprising a herbicidally effective amount of at least one compound of claim 1 and a carrier.

13. A method of killing plants comprising contacting plants with a herbicidally effective amount of at least one compound of claim 1.

14. The method of claim 13 wherein the compound is applied post-emergence.

15. The method of claim 13 wherein the compound is applied pre-emergence to the soil.

16. The method of claim 13 wherein the compound is N-(m-tolyl)-3-methoxy-crotonamide.

17. The method of claim 13 wherein the compound is 3-methoxy-crotonanilide.

* * * * *